United States Patent [19]
Rodarmel

[11] Patent Number: 5,241,708
[45] Date of Patent: Sep. 7, 1993

[54] RESTRAINING DEVICE

[76] Inventor: Pamela A. Rodarmel, 3422 Old Bruceville Rd., Vincennes, Ind. 47591

[21] Appl. No.: 988,853

[22] Filed: Dec. 10, 1992

[51] Int. Cl.⁵ .................. A41D 1/06; A41B 9/12
[52] U.S. Cl. .................................. 2/79; 2/227; 2/403; 2/406; 604/385.1; 604/396
[58] Field of Search .............. 2/1, 2, 46, 48, 49 R, 2/49 A, 69, 69.5, 111, 114, 79, 75, 80, 227, 400, 403, 406, 407, 408, DIG. 7; 604/358, 385.1, 393, 394, 396, 397, 398; 297/219, 485

[56] References Cited

U.S. PATENT DOCUMENTS

| | | |
|---|---|---|
| 2,283,362 | 5/1942 | Hamilton .................. 2/227 |
| 3,048,176 | 8/1962 | DeWoskin ................ 2/406 |
| 3,127,896 | 4/1964 | Puliafico ................... 2/227 |
| 3,180,336 | 4/1965 | Belt et al. ................. 2/80 |
| 3,641,997 | 2/1972 | Posey, Jr. . |
| 3,658,064 | 4/1972 | Pociluyko ................ 604/398 |
| 4,026,282 | 5/1977 | Thomas . |
| 4,170,991 | 10/1979 | Kella . |
| 4,274,159 | 6/1981 | Schmidt ................... 2/227 X |
| 4,351,340 | 9/1982 | McLeod .................. 2/406 X |
| 4,383,335 | 5/1983 | Slocum . |
| 4,427,408 | 1/1984 | Karami et al. ........... 2/406 |
| 4,676,554 | 6/1987 | Harlick et al. . |
| 4,795,176 | 1/1989 | Harrigan et al. . |
| 4,838,886 | 6/1989 | Kent ........................ 604/396 |
| 4,950,262 | 8/1990 | Takagi ................... 604/385.1 |
| 5,084,914 | 2/1992 | Hesch . |
| 5,185,009 | 2/1993 | Sitnam .................... 604/358 X |

OTHER PUBLICATIONS

1990–1991 Posey Safety & Health Care Products catalog, pp. 5, 6, 7, 8, 12.

Primary Examiner—Clifford D. Crowder
Assistant Examiner—Jeanette Chapman
Attorney, Agent, or Firm—Plews & Shadley

[57] ABSTRACT

A restraining device is disclosed for maintaining an individual in a seated position in a chair or similar and providing containment and absorption of waste materials produced by the individual. An external garment portion with appearance similar to ordinary clothing for the lower portion of the body has opposing, closeable side slots, and straps extending from rear waistband portions of the garment are removably disposable through loops attached to front waistband portions of the garment and tied behind the individual. A three-ply liner is attached to the interior of the garment, and a disposable, absorbent pad is removably attached to the interior of the liner.

20 Claims, 5 Drawing Sheets

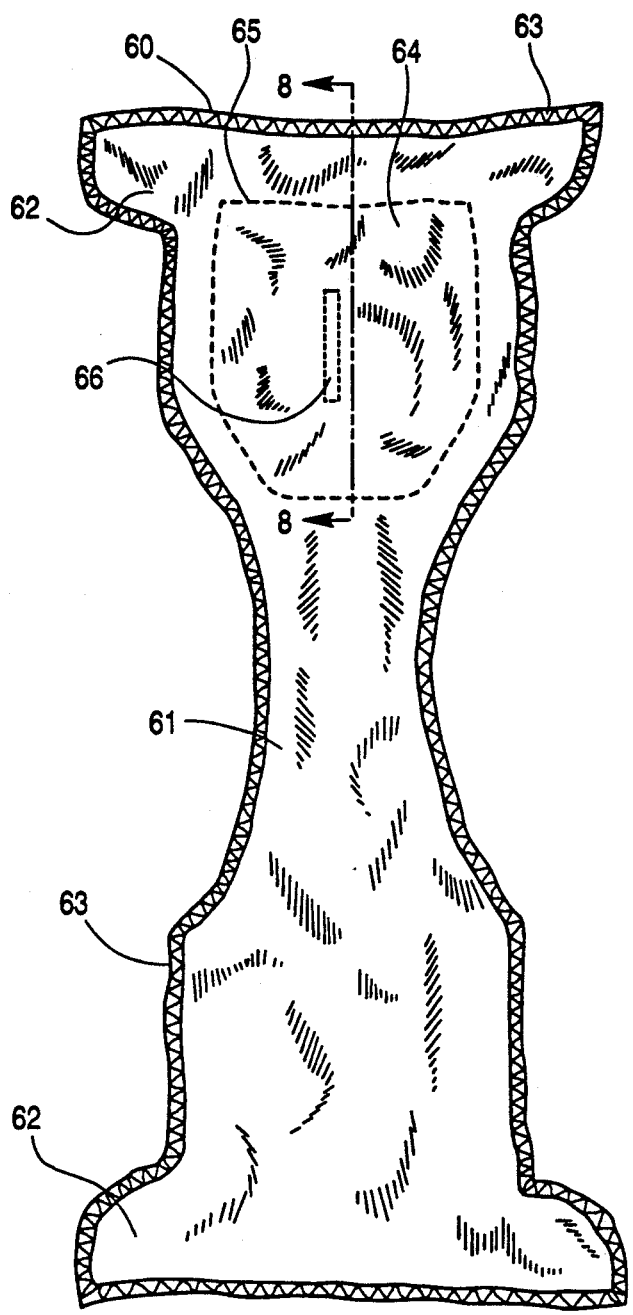
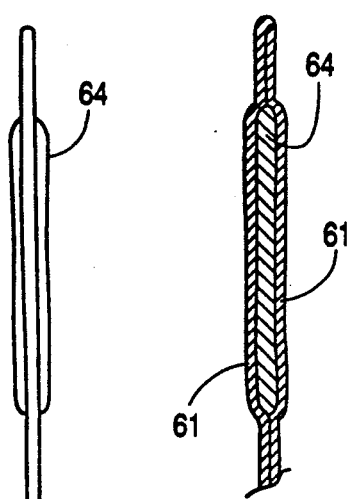
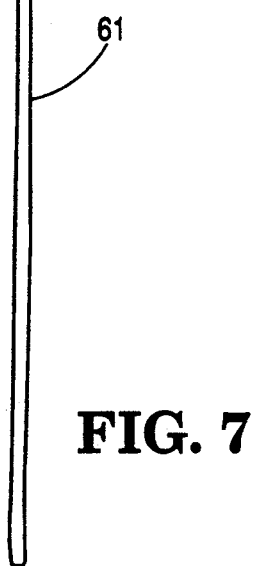
FIG. 6
FIG. 8
FIG. 7

RESTRAINING DEVICE

BACKGROUND OF THE INVENTION

1. Field of the Invention

Individuals who, due to illness or injury, have lost the capability of maintaining themselves in a seated position are also frequently incontinent. The present invention generally relates to devices for restraining such individuals so as to be maintained in a sitting position, and more specifically relates to devices for restraining individuals that are capable of use by incontinent persons, yet has an external appearance similar to ordinary clothing.

2. Description of the Prior Art

A common problem encountered in providing care to individuals who are incapable of remaining seated relates to the availability and efficiency of appropriate devices to help maintain such individuals in a sitting position. At the present time, it is a common practice to maintain these individuals in a seated position by tying the individual to a chair, wheelchair or other support by various makeshift devices that are frequently uncomfortable for the individual, and, in addition, serve to stigmatize the individual as one who requires the help of a device to remain seated. Moreover, individuals who have difficulty in remaining in a seated position are frequently incontinent. As a result, when such individuals are restrained in a sitting position, their waste materials may accumulate in and around their clothing and chair, resulting in an uncomfortable, embarrassing and unhygienic situation.

Devices for maintaining an individual in a sitting position are disclosed by U.S. Pat. Nos. 3,641,997, 4,026,282, 4,170,991, 4,676,554 and 4,795,176. Garments for incontinent individuals are disclosed by U.S Pat. Nos. 4,383,335 and 5,084,914.

Despite the availability of such devices, there exists a need in the art for a restraining device that is capable of comfortably maintaining an individual in a sitting position and provides for the collection of waste materials of the individual, yet minimizes the external indications that a restraining device is in use by providing an appearance similar to ordinary clothing.

SUMMARY OF THE INVENTION

In order to aid in the understanding of the present invention, it can be stated in essentially summary form that it is directed to a restraining device that has the external appearance similar to ordinary clothing for the lower portion of the body, yet is capable of securely and comfortably maintaining an individual in a seated position and containing waste materials produced by the individual in a removable, disposable portion.

It is an object of the present invention to provide a restraining device that is capable of securely maintaining an individual in a seated position.

It is another object of the present invention to provide a restraining device that is capable of maintaining an individual in a seated position in a dignified manner.

It is another object of the present invention to provide a restraining device that is capable of use by either gender.

It is another object of the present invention to provide a restraining device that is capable of use by persons of all ages.

It is another object of the present invention to provide a restraining device that is capable of preventing leakage of waste materials produced by an incontinent individual.

It is another object of the present invention to provide a restraining device that has absorbent, removable, disposable portion for the collection of waste materials produced by an incontinent individual.

It is another object of the present invention to provide a restraining device that is unobtrusive and has the external appearance similar to ordinary clothing for the lower portion of the body.

It is another object of the present invention to provide a restraining device that is comfortable to use.

It is still another object of the present invention to provide a restraining device that is capable of being easily and quickly removed from an individual, cleaned, and replaced.

It is yet another object of the present invention to provide a restraining device relatively inexpensive to manufacture.

Further objects and advantages of the present invention will be apparent from a study of the following portion of the specification, the claims, and the attached drawings.

BRIEF DESCRIPTION OF THE DRAWINGS

FIG. 6 is a plan view of the pad portion of a restraining device representing the present invention.

FIG. 7 is a side view of the pad portion of a restraining device representing the present invention.

FIG. 8 is a partial sectional view taken along line 8—8 of FIG. 6.

DESCRIPTION OF THE PREFERRED EMBODIMENTS

The following portion of the specification, taken in conjunction with the drawings, sets forth the preferred embodiments of the present invention. The embodiments of the invention disclosed herein are the best modes contemplated by the inventor for carrying out her invention in a commercial environment, although it should be understood that various modifications can be accomplished within the parameters of the present invention.

Figure 1:
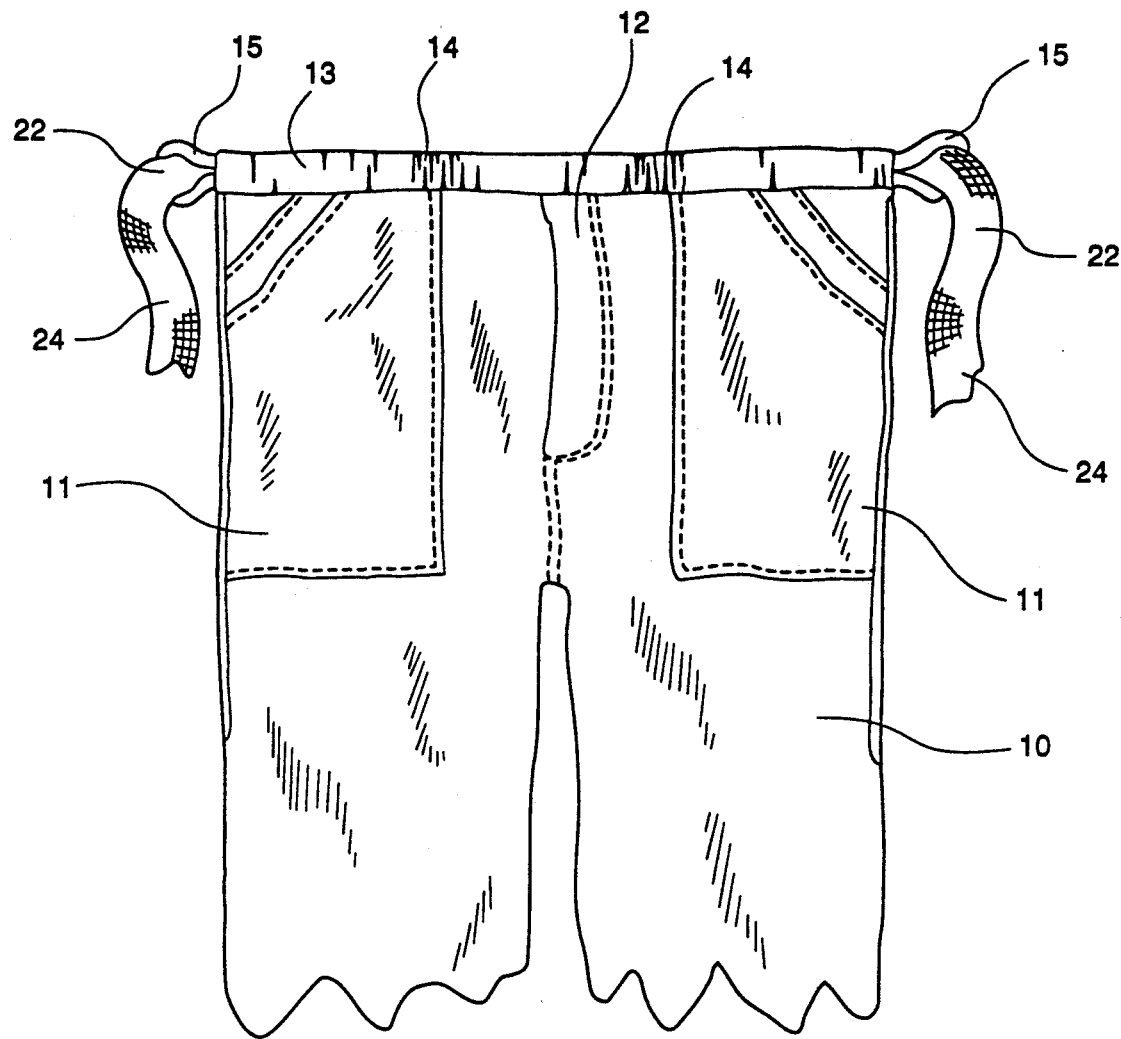
FIG. 1 is a front elevational view of a portion of the exterior of a restraining device representing the present invention.
Figure 2:
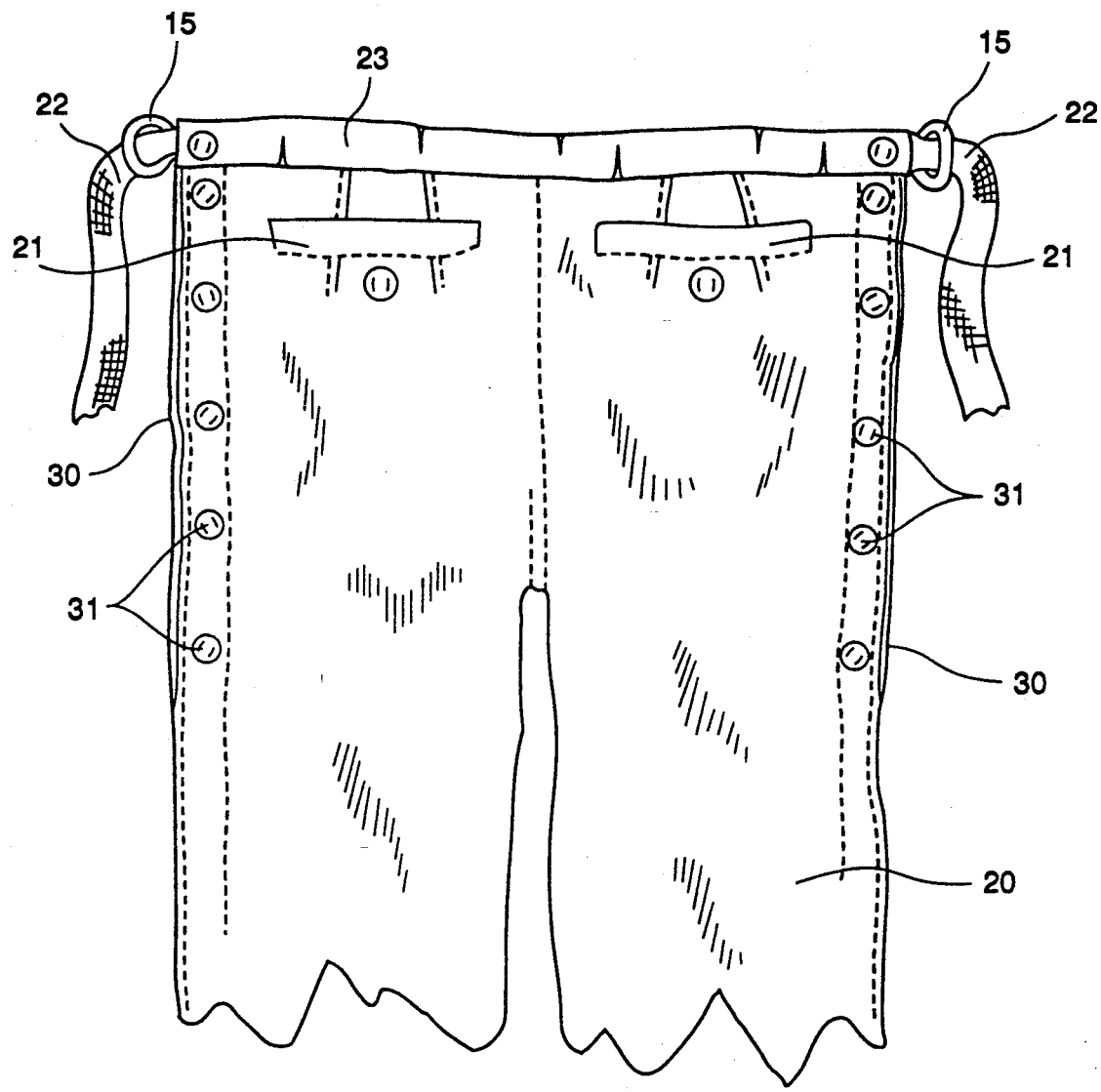
FIG. 2 is a rear elevational view of a portion of the exterior of a restraining device representing the present invention.
Figure 3:
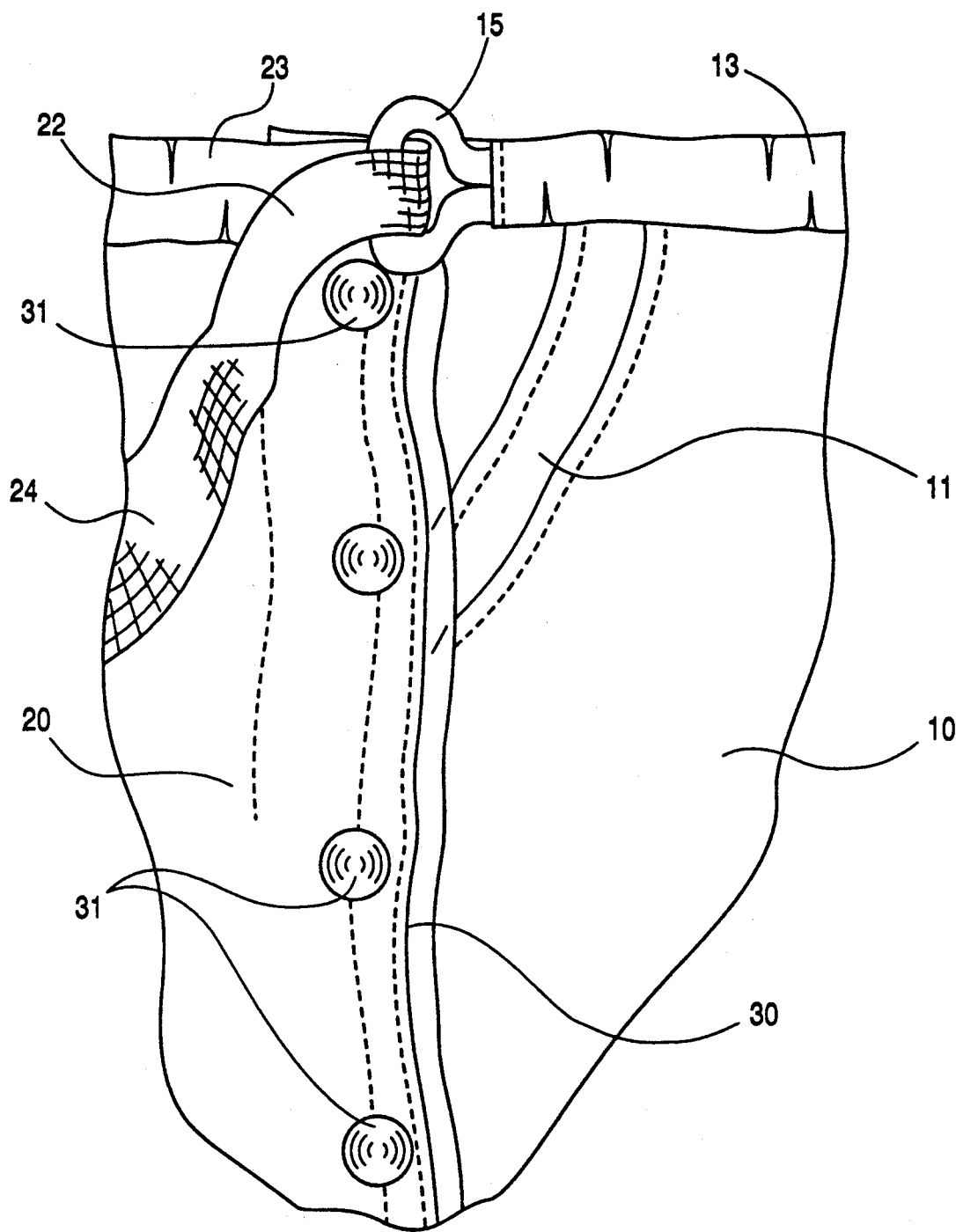
FIG. 3 is a side detail view of a portion of a restraining device representing the present invention.
Figures 4, 5:
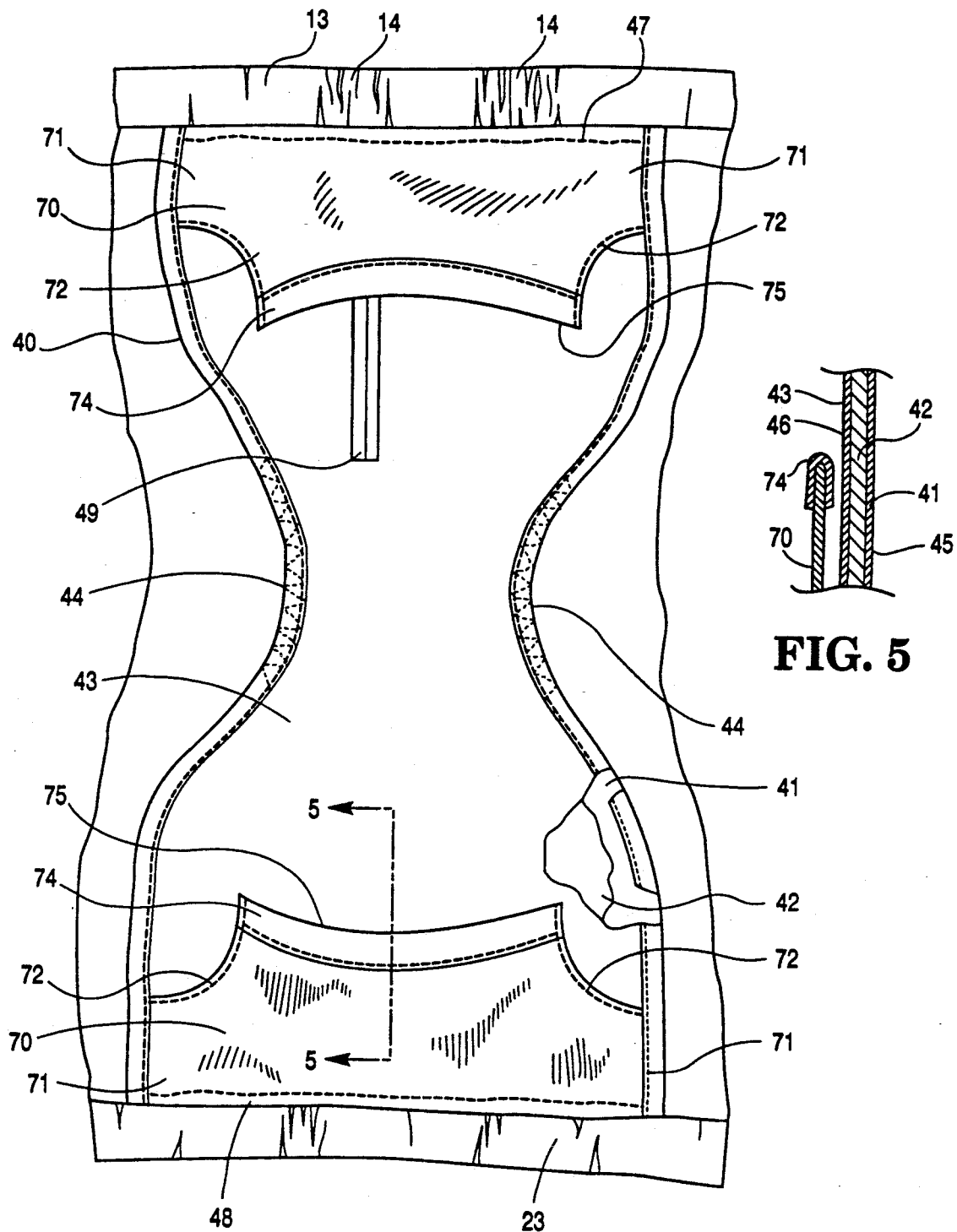
FIG. 4 is a plan view of the interior of a restraining device representing the present invention.
FIG. 5 is a partial sectional view taken along line 5—5 of FIG. 4.

Referring now to the drawings for a detailed description of the present invention, reference is first made to FIGS. 1, 2, and 3, depicting a garment front 10, formed to have the general appearance of the front of a pair of trousers, and has front pockets 11 and fly 12. Front waistband, not shown, is disposed interior to front waistband cover 13, and is formed from front waistband elastic segments interposed with front waistband resilient segments. As shown in FIGS. 1 and 4, front waistband cover 13 has waistband gathered portions 14, resulting from two symmetrically disposed front waistband elastic segments interior to front waistband cover 13. Disposed near each upper distal portion of garment front 10 is a loop 15, typically constructed of the same material as garment front 10. Each loop 15 is attached to front waistband cover 13 and to the front waistband, for instance by sewing.

As shown in FIG. 2, garment rear 20 is formed to have the general appearance of the rear of a pair of trousers, and has rear pockets 21. Elongated, resilient rear waistband 22 is disposed along and bisecting the upper edge of garment rear 20, with the central section of rear waistband 22 interior to rear waistband cover 23. Each rear waistband end 24 extends beyond rear waistband cover 23 and may be removably disposed through one of loops 15 and secured as hereinafter described. Garment front 10 is permanently attached, for instance by sewing, along the inseams and lower outseams to the corresponding portions of garment rear 20 in the typical manner of trousers. However, garment front 10 is not sewn to garment rear 20 along the upper outseams, so as to define two side slits 30, with one side slit 30 formed between each upper outseam of garment front 10 and the corresponding upper outseam of garment rear 20. The upper outseam of garment front 10 may be removably attached to the corresponding upper outseam of garment rear 20 by the use of snaps 31 attached along side slits 30, although it will be appreciated that side slits 30 may be closed by other commonly available means such as zippers, buttons or Velcro.

FIG. 4 depicts the interior of garment front 10 and garment rear 20 disposed in an opened configuration, that is, with snaps 31 unattached, rear waistband 22 removed from loops 14, and the upper portion of the present invention laid flat. Disposed interior to garment front 10 and garment rear 20 is generally rectangular liner 40, having a resilient, flexible, tear-resistant liner outer portion 41, a waterproof, resilient, flexible liner intermediate portion 42, and a soft, absorbent liner inner portion 43. The exterior surface 45 of liner outer portion 41 is disposed to form the exterior surface of liner 40, and the interior surface 46 of liner inner portion 43 is disposed to form the interior surface of liner 40. Disposed along and bisecting each longer edge of liner 40 is an elastic portion 44. Liner 40 is attached, for instance by sewing, along a first shorter edge 47 to the upper edge of garment front 10, the front waistband, and front waistband cover 13, and along a second shorter edge 48 to the upper edge of garment rear 20, rear waistband 22 and rear waistband cover 23. In this way, liner 40 is disposed adjacent to the interior surface of garment front 10 and garment rear 20. Liner fly opening 49 extends through liner outer portion 41, liner intermediate portion 42, and liner inner portion 43, and is disposed to correspond with the location of fly 12.

Shown in FIGS. 6, 7, and 8 is soft, disposable, two-ply, absorbent pad 60 having narrowed pad midsection 61, widened pad ends 62, and surrounding band 63. In order to provide additional absorbent capacity, extra pad 64 is disposed between the plies of pad 60, and held in place by pad stiching 65. In addition, catheter stitching 66 extends through pad 60 in the manner of an unopened buttonhole, so that in the event an individual requires the use of a catheter, a catheter slit, not shown, may be cut through pad 60 within catheter stitching 66. Although the location of extra pad 64 shown in FIG. 6 corresponds to use of the present invention by a male, it will be understood that extra pad 64 may be reduced in size and extra pad 64 and catheter stitching 66 disposed proximate to pad midsection 61 for use of the present invention by a female.

As shown in FIGS. 4 and 5, a pair of opposing, pockets 70 formed of a soft, absorbent material are disposed adjacent to liner inner portion 43 and attached, for instance by sewing, along first shorter edge 47, second shorter edge 48, pocket distal sides 71, and pocket arcuate portions 72. A soft, absorbent pocket band 74 is disposed along each curved pocket open end 75. In this way, each widened pad end 62 may be removably placed within one of pockets 70.

The present invention is readied for use by placement of pad 60 adjacent to liner inner portion 43 and within pockets 70. With snaps 31 opened, the lower extremities of an individual are placed through the lower portion of the present invention. Snaps 31 are then closed, and each rear waistband end 24 is disposed toward garment front 10 and through one of loops 15. After the individual is placed in a sitting position in a chair or similar, each rear waistband end 24 is may be folded backwards, toward garment rear 20, effectively attaching garment front 10 to garment rear 20. Rear waistband ends 24 may then be removably attached to one another behind the chair, for instance by tying rear waistband ends 24 together or by the use of a buckle, snap or similar. In this way, the individual is maintained in a sitting position in a comfortable manner where slight movements and breathing are facilitated due to the presence of elastic portions 44, while the fact that the individual cannot maintain himself or herself in a sitting position without the use of an external device is substantially disguised. Pad 60 acts to absorb waste materials, and elastic portions 44 act to prevent leakage of any waste materials not absorbed by pad 60.

In addition, the present invention may be used by individuals who are incontinent but have not lost the capability to remain in a seated position by removing that portion of each rear waistband end 22 projecting outside rear waistband cover 23. Similarly, the present invention may be worn by an individual who is continent but requires assistance to remain in a seated position, by use of the present invention without pad 60.

It will be understood that garment front 10 and garment rear 20 may be formed to have the general appearance of items of clothing other than a pair of trousers, and that such a change in general appearance may in some instances require modifications of the present invention as hereinabove described. For instance, garment front 10 and garment rear 20 may be formed to have the general appearance of a skirt, so that fly 12 may be omitted from garment front 10 and liner fly opening 49 may be omitted from liner 40.

The present invention having been described in its preferred embodiment, it is clear that it is susceptible to numerous modifications and embodiments within the ability of those skilled in the art and without the exercise of the inventive faculty. Accordingly, the scope of the present invention is defined by the scope of the following claims.

What is claimed is:

1. Restraining device comprising:
a lower body garment having a garment front, a garment rear, a pair of straps, and a pair of loops, said garment front attached to said garment rear so as to define a pair of opposing, open-ended side slits formed between each upper distal portion of said garment front and the corresponding upper distal portion of said garment rear, each of said straps attached to an upper distal corner of said garment rear, and each of said loops attached to an upper distal corner of said garment front so that each of said straps may be removably disposed through one of said loops;

means for removably attaching each upper distal portion of said garment front to the corresponding upper distal portion of said garment rear so that said side slits may be closed and opened;

a generally rectangular liner;

means for attaching a first shorter edge of said liner to the upper edge of said garment front and a second shorter edge of said liner to the upper edge of said garment rear so that said liner is disposed adjacent to the interior surface of said garment;

a disposable pad; and means for removably attaching said pad to the interior surface of said liner.

2. Restraining device as defined in claim 1, wherein said garment further comprises a plurality of elastic segments linearly disposed along the upper edge of said garment front.

3. Restraining device as defined in claim 1, wherein said means for attaching said first shorter edge of said liner to the upper edge of said garment front and said second shorter edge of said liner to the upper edge of said garment rear comprises sewing said first shorter edge of said liner to the upper edge of said garment front and sewing said second shorter edge of said liner to the upper edge of said garment.

4. Restraining device as defined in claim 1 wherein said means for removably attaching each upper distal portion of said garment front to the corresponding upper distal portion of said garment rear comprises hook and loop fasteners attached along said side slits.

5. Restraining device as defined in claim 1, wherein said means for removably attaching each upper distal portion of said garment front to the corresponding upper distal portion of said garment rear comprises a plurality of snaps attached along said side slits.

6. Restraining device as defined in claim 1, wherein said means for removably attaching each upper distal portion of said garment front to the corresponding upper distal portion of said garment rear comprises a plurality of buttons and buttonholes attached along said side slits.

7. Restraining device as defined in claim 1, wherein said means for removably attaching each upper distal portion of said garment front to the corresponding upper distal portion of said garment rear comprises a zipper attached along said side slits.

8. Restraining device as defined in claim 1, wherein said liner further comprises a resilient, flexible, tear-resistant liner outer portion, a waterproof, resilient, flexible liner intermediate portion, a soft, absorbent liner inner portion, and a pair of opposing, elastic portions, the exterior surface of said liner outer portion forming the exterior surface of said liner, the interior surface of said liner inner portion forming the interior surface of said liner, and one of said elastic portions disposed along and bisecting each longer edge of said liner.

9. Restraining device as defined in claim 8, wherein said means for removably attaching said pad to the interior surface of said liner comprises a pair of opposing pockets, each of said pockets disposed adjacent to the interior surface of said liner inner portion.

10. Restraining device comprising:

a lower body garment having a garment front, a garment rear, a pair of straps, a pair of loops, and a plurality of elastic segments, said garment front attached to said garment rear so as to define a pair of opposing, open-ended side slits, one of said side slits formed between each upper distal portion of said garment front and the corresponding upper distal portion of said garment rear, each of said straps attached to an upper distal corner of said garment rear, each of said loops attached to an upper distal corner of said garment front so that each of said straps may be removably disposed through one of said loops, and said elastic segments linearly disposed along the upper edge of said garment front;

means for removably attaching each upper distal portion of said garment front to the corresponding upper distal portion of said garment rear so that said side slits may be closed and opened;

a generally rectangular liner having a resilient, flexible, tear-resistant liner outer portion, a waterproof, resilient, flexible liner intermediate portion, a soft, absorbent liner inner portion, and a pair of opposing, elastic portions, the exterior surface of said liner outer portion forming the exterior surface of said liner, the interior surface of said liner inner portion forming the interior surface of said liner, one of said elastic portions disposed along and bisecting each longer edge of said liner, and said liner attached to said garment along a first liner shorter edge to the upper edge of said garment front, and along a second liner shorter edge to the upper edge of said garment rear, so that said liner is disposed adjacent to the interior surface of said garment;

a disposable pad; and a pair of opposing pockets for removably attaching said pad to the interior surface of said liner, each of said pockets disposed adjacent to the interior surface of said liner inner portion.

11. Restraining device as defined in claim 10, wherein said means for removably attaching each upper distal portion of said garment front to the corresponding upper distal portion of said garment rear comprises Velcro attached along said side slits.

12. Restraining device as defined in claim 10, wherein said means for removably attaching each upper distal portion of said garment front to the corresponding upper distal portion of said garment rear comprises a plurality of snaps attached along said side slits.

13. Restraining device as defined in claim 10, wherein said means for removably attaching each upper distal portion of said garment front to the corresponding upper distal portion of said garment rear comprises a plurality of buttons and buttonholes attached along said side slits.

14. Restraining device as defined in claim 10, wherein said means for removably attaching each upper distal portion of said garment front to the corresponding upper distal portion of said garment rear comprises a zipper attached along said side slits.

15. Restraining device comprising:

a lower body garment having a garment front, a garment rear, an elongated, resilient rear waistband, a pair of loops, and a front waistband, said garment front attached to said garment rear so as to define a pair of opposing, open-ended side slits, one of said side slits formed between each upper distal portion of said garment front and the corresponding upper distal portion of said garment rear, said rear waistband attached along and bisecting the upper edge of said garment rear and extending beyond said garment rear, each of said loops attached to an upper distal corner of said garment front so that each end of said rear waistband may be removably disposed through one of said loops;

means for removably attaching each upper distal portion of said garment front to the corresponding upper distal portion of said garment rear so that said side slits may be closed and opened;

means for removably attaching together the ends of said rear waistband;

a generally rectangular liner having a resilient, flexible, tear-resistant liner outer portion, a waterproof, resilient, flexible liner intermediate portion, a soft, absorbent liner inner portion, and a pair of opposing, elastic portions, the exterior surface of said liner outer portion forming the exterior surface of said liner, the interior surface of said liner inner portion forming the interior surface of said liner, one of said elastic portions disposed along and bisecting each longer edge of said liner, and said liner attached to said garment along a first liner shorter edge to the upper edge of said garment front and said front waistband, and along a second liner shorter edge to the upper edge of said garment rear and said rear waistband, so that said liner is disposed adjacent to the interior surface of said garment;

a disposable pad; and a pair of opposing pockets for removably attaching said pad to the interior surface of said liner, each of said pockets disposed adjacent to the interior surface of said liner inner portion.

16. Restraining device as defined in claim 15, wherein said front waistband comprises a plurality of front waistband elastic segments interposed with a plurality of front waistband resilient segments.

17. Restraining device as defined in claim 16, wherein said means for removably attaching each upper distal portion of said garment front to the corresponding upper distal portion of said garment rear comprises hook and loop fasteners attached along said side slits.

18. Restraining device as defined in claim 16, wherein said means for removably attaching each upper distal portion of said garment front to the corresponding upper distal portion of said garment rear comprises a plurality of snaps attached along said side slits.

19. Restraining device as defined in claim 16, wherein said means for removably attaching each upper distal portion of said garment front to the corresponding upper distal portion of said garment rear comprises a plurality of buttons and buttonholes attached along said side slits.

20. Restraining device as defined in claim 16, wherein said means for removably attaching each upper distal portion of said garment front to the corresponding upper distal portion of said garment rear comprises a zipper attached along said side slits.

* * * * *